United States Patent [19]
Labroo et al.

[11] Patent Number: 5,698,672
[45] Date of Patent: Dec. 16, 1997

[54] SYNTHETIC CALCITONIN MIMETICS

[75] Inventors: Virender M. Labroo, Mill Creek; Stephanie Beigel, Seattle, both of Wash.

[73] Assignee: ZymoGenetics, Inc., Seattle, Wash.

[21] Appl. No.: 416,601

[22] Filed: Apr. 4, 1995

[51] Int. Cl.$^6$ .......................... A61K 31/06; A61K 38/10; C07K 7/06; C07K 7/00
[52] U.S. Cl. .......................... 530/326; 530/327; 530/328; 514/13; 514/14; 514/15
[58] Field of Search .................. 514/13, 14, 15; 530/326, 327, 328

[56] References Cited

FOREIGN PATENT DOCUMENTS 2218102  11/1989  United Kingdom .
2257908   1/1993  United Kingdom .

OTHER PUBLICATIONS

Ngo et al., in The Protein Folding Problem and the Tertiary Structure Prediction, 1994, Merz et al (Ed.), Birkhauser, Boston, MA, pp. 433 and 492–495.

Inoue A. et al. Structure/activity relationship of eel calcitonin. eur. J. Biochem., 201, 607–614, 1991.

D'Santos C.S. et al. Biologically active derivatizable salmon calcitonin analogs:design, synthesis, and application. Endocrinology, 123(3), 1483–1488, 1988.

Kaiser E.T. The design of peptides and proteins. Annals NY Acad. Sci. 471, 233–238, 1986.

Yates, et al., *Endocrinology* 126 (6): 2845–2849, 1990.

Orlowski et al., *Eur. J. Biochem.* 162: 399–402, 1987.

Rinehart et al., *J. Am. Chem. Soc.* 103: 6517–6520, 1981.

Moe et al., *Biochemistry* 24: 1971–1976, 1985.

*Primary Examiner*—Cecilia J. Tsang
*Assistant Examiner*—Michael Borin
*Attorney, Agent, or Firm*—Susan E. Lingenfelter

[57] ABSTRACT

The invention provides synthetic calcitonin mimetics. The mimetics of the present invention may include modifications that further enhance desired characteristics, such as oral bioavailability, while maintaining or enhancing inhibition of bone resorption. Related pharmaceutical compositions and methods are also disclosed.

15 Claims, No Drawings

SYNTHETIC CALCITONIN MIMETICS

BACKGROUND OF THE INVENTION

Bone is a dynamic tissue, and homeostasis in the adult skeleton requires a balance between bone resorption and bone formation. Osteoclasts and osteoblasts play a key role in this balance, with osteoclasts initiating bone resorption and osteoblasts synthesizing and depositing new bone matrix. Imbalances in bone homeostasis are associated with such conditions as osteoporosis, Paget's disease, and hyperparathyroidism.

The activities of osteoclasts and osteoblasts are regulated by complex interactions between systemic hormones and the local production of growth factors and cytokines. Calcitonin, a peptide hormone secreted by the thyroid and thymus of mammals, plays an important role in maintaining bone homeostasis. Calcitonin inhibits bone resorption through binding and activation of a specific calcitonin receptor on osteoclasts (*The Calcitonins—Physiology and Pharmacology*, Azria (ed.), Karger, Basel, Su., 1989), with a resultant decrease in the amount of calcium released by bone into the serum. This inhibition of bone resorption has been exploited, for instance, by using calcitonin as a treatment for osteoporosis, a disease characterized by a decrease in the skeletal mass often resulting in debilitating and painful fractures. Calcitonin is used in the treatment of Paget's disease as well, where it also provides rapid relief from bone pain, which is frequently the primary symptom associated with this disease. This analgesic effect has also been demonstrated in patients with osteoporosis, metastatic bone disease, and has been reported to relieve pain associated with diabetic neuropathy, cancer, migraine and posthysterectomy. Reduction in bone pain occurs before the reduction of bone resorption.

Salmon calcitonin has been shown to be considerably more effective in arresting bone resorption than human forms of calcitonin. There are several hypotheses to explain this observation which include: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites.

Despite the advantages associated with the use of salmon calcitonin in humans, there are also disadvantages. For treatment of osteoporosis, for instance, the average cost can exceed $75 a week and involve daily prophylactic administration for 5 or more years. In the United States, calcitonin must be administered by injection, and since the disease indications for this drug are not usually life threatening, patient compliance can be low. In addition, some patients develop antibodies to non-human calcitonin. Therefore, mimetics of human calcitonin that are potent inhibitors of bone resorption, less expensive for the consumer, more convenient to administer (i.e., orally), and non-immunogenic are needed.

SUMMARY OF THE INVENTION

The present invention provides isolated compounds that are synthetic calcitonin mimetics. As used herein, the term "calcitonin mimetic" refers to any compound with the ability to mimic the interaction of calcitonin on its receptor and, by such interaction, stimulate G-protein-mediated activation of adenyl cyclase. The synthetic calcitonin mimetics of the present invention are derived from a native calcitonin mimetic, 2807 B, described in pending U.S. patent application Ser. No. 08/416,602. Calcitonin mimetics of the present invention were synthesized containing modifications to further enhance desired characteristics, such as oral bioavailability, while maintaining or enhancing the inhibition of bone resorption.

Prior to setting forth the invention, it may be helpful to an understanding thereof to set forth definitions of certain terms to be used hereinafter:

| | |
|---|---|
| 2-aminoisobutyric acid | Aib |
| Alanine | Ala |
| Allo-Threonine | Allo-Thr |
| Arginine | Arg |
| Asparagine | Asn |
| Aspartic Acid | Asp |
| Cysteine | Cys |
| Glutamine | Gln |
| Glutamic acid | Glu |
| Glycine | Gly |
| Histidine | His |
| Isoleucine | Ile |
| Isovaline | Iva |
| Leucine | Leu |
| Lysine | Lys |
| Methionine | Met |
| Ornithine | Orn |
| Penicillamine | Pen |
| Phenylalanine | Phe |
| Proline | Pro |
| Serine | Ser |
| Threonine | Thr |
| Tryptophan | Typ |
| Tyrosine | Tyr |
| Valine | Val |

Alkyl refers to a saturated acyclic hydrocarbon radical.

Alkenyl refers to a radical of an unsaturated, branched or unbranched acyclic hydrocarbon having at least one double bond.

Alkynyl refers to a radical of an unsaturated, branched or unbranched acyclic hydrocarbon having at least one triple bond.

Mono- or poly-cycloalkyl refers to a radical of a saturated hydrocarbon having one ring (mono) or more than one (poly) ring.

Mono- or poly-aryl refers to a radical of an aromatic hydrocarbon containing one (mono) or more than one (poly) aromatic ring.

Mono- or poly-heteroaryl refers to a radical of an aromatic hydrocarbon containing at least one heteroatom, which is used here to mean an atom other than carbon, most commonly referring to nitrogen (N), oxygen (O) or sulfur (S).

α amino acid refers to an amino acid of the general formula R—CHNH$_2$—COOH, with the amino group (NH$_2$) in the α position. L-amino acids are those having the α amino group to the left of the α carbon atom, and D amino acids have the α amino group to the right of the α carbon atom.

α-alkylated α amino acid refers to an α amino acid having an alkyl group substituent on the α carbon atom. α-alkylated amino acids include Aib, Iva and α-methyl serine.

Aliphatic amino acid refers to an α amino acid wherein the side chain R group is hydrogen or a straight or branched chain substituent. These amino acids contain no aromatic rings. Aliphatic amino acids include Ala, Arg, Asn, Asp, Cys, Gln, Glu, Gly, His, Ile, Leu, Lys, Met, Pro, Ser, Thr and Val.

Aromatic amino acid refers to an α-amino acid wherein the side chain R group contains an aromatic ring. Aromatic amino acids include Phe, Trp, and Tyr.

β-branched amino acid refers to an α amino acid wherein the side chain β carbon atom has a substituent. β-branched amino acids include Ile, Thr, Val, and allo-Thr.

H-bond donor amino acid refers to an amino acid which can donate a hydrogen bond, such as from —NH or —OH groups. H-bond donor amino acids include Arg, Asn, Gln, His, Lys, Orn, Ser and Thr.

Unnatural amino acids are those which are derived from one of the 20 standard α amino acids which have been modified after protein synthesis, or which have a chemical structure of the side chain(s) different from that of the standard amino acids. Within the present invention, unnatural amino acids can be chemically synthesized, or preferably, are commercially available. Unnatural amino acids include pipecolic acid, thiazolidine carboxylic acid, 3- and 4-hydroxyproline, dehydroproline, 3- and 4-methylproline, and 3,3-dimethylproline. Unnatural aromatic amino acids may include an aromatic ring.

The present invention provides compounds of the formula W-X-Y, wherein:

W is
  hemisuccinimide, or
  $R_1$—CO—, wherein $R_1$ is selected from the group consisting of:
  hydrogen;
  linear or branched alkyl, alkenyl, or alkynyl of not more than 32 carbon atoms;
  unsubstituted mono- or poly-cycloalkyl or mono- or poly-cycloalkylmethyl of not more than 20 carbon atoms, not more than 4 rings, each ring having 5–6 carbon atoms;
  unsubstituted mono- or poly-aryl or mono- or poly-arylmethyl of not more than 20 carbon atoms, not more than 4 rings, each ring having 5–6 carbon atoms; and
  unsubstituted mono- or poly-heteroaryl or mono- or poly-heteroarylmethyl of not more than 20 atoms, not more than 4 rings, each ring having 5–6 ring atoms and not more than 4 heteroatoms, in which the heteroatoms are selected from the group consisting of: N, O, and S;

X is
  a peptide of 3–18 amino acid residues having the formula:
  $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$ (SEQ ID NO 1) wherein:
  $Xaa_1$ is D- or L-Arg,
    D- or L-Lys,
    D- or L-Orn, or
    absent;
  $Xaa_2$ is
    a D- or L- aromatic amino acid,
    an unnatural aromatic amino acid,
    Cys,
    Pen, or
    absent,
  with the proviso that when $Xaa_2$ is Cys or Pen, $Xaa_8$ is Cys or Pen;
  $Xaa_3$ is
    an α-alkylated α amino acid,
    a β-branched amino acid, or
    absent;
  $Xaa_4$ is
    Gln,
    Asn,
    His, or
    a substituted amide ($R_2$—NH-Z), wherein Z is an α- or γ-acyl radical of Asn or Gln, and $R_2$ is selected from a group consisting of:
    polyethylene glycol (PEG);
    linear or branched alkyl, alkenyl, or alkynyl of not more than 32 carbon atoms;
    unsubstituted mono- or poly-cycloalkyl or mono- or poly-cycloalkylmethyl of not more than 20 carbon atoms, not more than 4 rings, each ring having 5–6 carbon atoms;
    unsubstituted mono- or poly-aryl or mono- or poly-arylmethyl of not more than 20 carbon atoms, not more than 4 rings, each ring having 5–6 carbon atoms; and
    unsubstituted mono- or poly-heteroaryl or mono- or poly-heteroarylmethyl of not more than 20 atoms, not more than 4 rings, each ring having 5–6 ring atoms, and not more than 4 heteroatoms, wherein the heteroatoms are selected from the group consisting of: N, O, and S;
  $Xaa_5$ is
    an α-alkylated α amino acid, or
    a D-amino acid;
  $Xaa_6$ is
    a β-branched amino acid, or
    an aliphatic amino acid;
  $Xaa_7$ is
    a β-branched amino acid,
    an H-bond donor amino acid, or
    absent;
  $Xaa_8$ is
    an α-alkylated α amino acid,
    a D-amino acid,
    Pen,
    Cys, or
    absent,
  with the proviso that when $Xaa_8$ is Cys or Pen, $Xaa_2$ is Cys or Pen;
  $Xaa_9$ is
    a β-branched amino acid,
    an aliphatic amino acid, or
    absent;
  $Xaa_{10}$ is
    an α-alkylated α amino acid,
    a D-amino acid, or
    absent;
  $Xaa_{11}$ is
    Pro,
    pipecolic acid,
    thiazolidine carboxylic acid,
    3- or 4-hydroxyproline,
    dehydroproline,
    3- or 4-methylproline,
    3,3-dimethylproline,
    N-alkyl alanine, or
    absent;
  $Xaa_{12}$ is
    Gln,
    Asn,
    Arg,
    His,
    absent, or
    a substituted amide ($R_2$—NH-Z), wherein Z is an α- or γ-acyl radical of Asn or Gln, and $R_2$ is selected from a group consisting of:
    polyethylene glycol (PEG);
    linear or branched alkyl, alkenyl, or alkynyl of not more than 32 carbon atoms;
    unsubstituted mono- or poly-cycloalkyl or mono- or poly-cycloalkylmethyl of not more than 20 carbon atoms, not more than 4 rings, each ring having 5–6 carbon atoms;

unsubstituted mono- or poly-aryl or mono- or poly-arylmethyl of not more than 20 carbon atoms, not more than 4 rings, each ring having 5–6 carbon atoms; and unsubstituted mono- or poly-heteroaryl or mono- or poly-heteroarylmethyl of not more than 20 atoms, not more than 4 rings, each ring having 5–6 ring atoms, and not more than 4 heteroatoms, wherein the heteroatoms are selected from the group consisting of: N, O, and S;

$Xaa_{13}$ is
an α-alkylated α amino acid;
a D-amino acid; or
absent;

$Xaa_{14}$ is
Pro,
pipecolic acid,
thiazolidine carboxylic acid,
3- or 4-hydroxyproline,
3- or 4-methylproline,
dehydroproline,
3,3-dimethylproline,
N-alkyl alanine, or
absent;

$Xaa_{15}$ is
an α-alkylated α-amino acid,
a D-amino acid; or
absent;

$Xaa_{16}$ is
Pro,
pipecolic acid,
thiazolidine carboxylic acid,
3- or 4-hydroxyproline,
3- or 4-methylproline,
dehydroproline,
3,3-dimethylproline,
N-alkyl alanine, or
absent;

$Xaa_{17}$ is
a D- or L-aromatic amino acid;
an unnatural aromatic amino acid; or
absent;

$Xaa_{18}$ is
Asp,
Glu or
absent;

Y is
hemisuccinimide,
$R_3$-Z,
wherein, when Z is an aminoacyl radical of $Xaa_{17}$, $R_3$ is:
OH,
$NH_2$,
NH-PEG, or
$NHCH_2(CH_2)_n$—$R_4$, wherein n=32 and R4 is hydrogen or an α amino acid; or wherein, when Z is an α-aminoalkyl radical of $Xaa_{17}$, $R_3$ is:
COOH,
$CONH_2$,
$CH_2OH$
CONH-PEG, or
$CONHCH_2(CH_2)_n$—R4, wherein n=32 and R4 is hydrogen or an α amino acid; or a substituted amide ($R_2$—NH-Z), wherein Z is an α- or γ-acyl radical of $Xaa_{18}$, and $R_2$ is selected from a group consisting of:

polyethylene glycol (PEG);

linear or branched alkyl, alkenyl, or alkynyl of not more than 32 carbon atoms;

unsubstituted mono- or poly-cycloalkyl or mono- or poly-cycloalkylmethyl of not more than 20 carbon atoms, not more than 4 rings, each ring having 5–6 carbon atoms;

unsubstituted mono- or poly-aryl or mono- or poly-arylmethyl of not more than 20 carbon atoms, not more than 4 rings, each ring having 5–6 carbon atoms; and unsubstituted mono- or poly-heteroaryl or mono- or poly-heteroarylmethyl of not more than 20 atoms, not more than 4 rings, each ring having 5–6 ring atoms, and not more than 4 heteroatoms, wherein the heteroatoms are selected from the group consisting of: N, O, and S.

A second aspect of the current invention provides a compound according to claim 1, wherein a linear or branched alkyl, alkenyl or alkynyl is selected from the group consisting of: methyl, ethyl, propyl, isopropyl, butyl, lauryl, myristyl, palmitoyl, stearoyl, and valaryl.

The current invention further provides a compound according to claim 2, wherein the linear or branched alkyl, alkenyl or alkynyl is lauryl.

Within another aspect, the current invention provides a compound according to claim 1, wherein an unsubstituted mono- or poly-cycloalkyl or mono- or poly-cycloalkylmethyl is selected from the group consisting of: cyclopentyl, cyclohexyl, cyclobutyl, cyclopropyl, cycloheptyl, decahydronaphthyl and admantyl.

The current invention further provides a compound according to claim 4, wherein the unsubstituted mono- or poly-cycloalkyl or mono- or poly-cycloalkylmethyl is cyclohexyl or admantyl.

Within yet another aspect, the current invention provides a compound according to claim 1, wherein an unsubstituted mono- or poly-aryl or mono- or poly-arylmethyl is selected from the group consisting of: benzyl, phenyl, biphenyl, naphthyl, anthranyl and fluorenyl.

The current invention further provides a compound according to claim 6, wherein the unsubstituted mono- or poly-aryl or mono- or poly-arylmethyl is phenyl, naphthyl or biphenyl.

Within still another aspect, the current invention provides a compound according to claim 1, wherein an unsubstituted mono- or poly-heteroaryl or mono- or poly-arylmethyl is selected from the group consisting of: indolyl, imidazolyl, furanyl, thiophenyl, benzofuranyl, pyrrolyl, benzimidazolyl, pyridinyl, bipyridinyl, benzothiophenyl, quinolinyl, tetrahydroisoquinolinyl, pyridylmethyl and imidazolylmethyl.

The current invention further provides a compound according to claim 8, wherein the unsubstituted mono- or poly-heteroaryl or mono- or poly-arylmethyl is furanyl or imidazolyl.

A third aspect of the current invention provides a compound according to claim 1, wherein the aromatic ring of an unnatural aromatic amino acid is selected from the group consisting of: thiazolyl, thiophenyl, pyrazolyl, benzimidazolyl, naphthyl, furanyl, pyrrolyl, and pyridyl.

The current invention further provides a compound according to claim 10, wherein the unnatural aromatic amino acid is β-2-thienyl-alanine, β-3-thienyl-alanine, β-1-naphthyl-alanine, β-2-naphthyl-alanine, β-2-pyridyl-alanine or β-3-pyridyl-alanine.

Within a fourth aspect, the current invention provides acompound according to claim 1, wherein the β-branched amino acid is selected from the group consisting of: Val, Ile, Thr, and allo-Thr.

Within a fifth aspect, the current invention provides a compound according to claim 1, wherein the aliphatic amino acid is Leu or Ala.

Within a sixth aspect, the current invention provides a compound according to claim 1, wherein the H-bond donor amino acid is selected from the group consisting of: Gln, Asn, His, Ser and Thr.

Within a seventh aspect, the current invention provides a compound according to claim 1, wherein:

W is hemisuccinimide, or $R_1$—CO—, wherein $R_1$ is methyl or hydrogen;
$Xaa_1$ is Arg, or
absent;
$Xaa_2$ is
Trp, or
Cys,
with the proviso that when $Xaa_2$ is Cys, $Xaa_8$ is also Cys;
$Xaa_3$ is
Aib,
Iva,
Val, or
Ile;
$Xaa_4$ is
Gln,
Asn, or
His;
$Xaa_5$ is
Aib, or
Iva;
$Xaa_6$ is
Ile, or
Leu;
$Xaa_7$ is
Thr,
allo-Thr, or
Ser;
$Xaa_8$ is
Aib, or
Cys,
with the proviso that when $Xaa_8$ is Cys, $Xaa_2$ is also Cys;
$Xaa_9$ is
Leu, or
Ile;
$Xaa_{10}$ is
Aib, or
Iva;
$Xaa_{11}$ is
Pro,
4-hydroxyproline, or
absent;
$Xaa_{12}$ is
Gln,
Asn,
Arg,
His, or
absent;
$Xaa_{13}$ is
Aib,
Iva, or
absent;
$Xaa_{14}$ is
Pro,
4-hydroxyproline, or
absent;
$Xaa_{15}$ is
Aib,
Iva, or
absent;
$Xaa_{16}$ is
Pro,
4-hydroxyproline, or
absent;
$Xaa_{17}$ is
Phe, or
absent;
$Xaa_{18}$ is
Asp, or
absent; and
Y is
$R_3$-Z,
wherein, when Z is an aminoacyl radical of $Xaa_{17}$, $R_3$ is:
OH,
$NH_2$,
NH-PEG, or
$NHCH_2(CH_2)_n$—R4, wherein n=32 and R4 is hydrogen or an α amino acid; or
wherein, when Z is an α-aminoalkyl radical of $Xaa_{17}$, $R_3$ is:
COOH,
$CONH_2$,
$CH_2OH$
CONH-PEG, or
$CONHCH_2(CH_2)_n$—R4, wherein n=32 and R4 is hydrogen or an α amino acid.

A preferred aspect of the current invention provides a compound according to claim 15 wherein:

$Xaa_1$ is absent;
$Xaa_2$ is Trp or Cys, with the proviso that when $Xaa_2$ is Cys, $Xaa_8$ is also Cys;
$Xaa_3$ is Aib or Val;
$Xaa_4$ is Gln, Asn, or His;
$Xaa_5$ is Aib;
$Xaa_6$ is Ile or Leu;
$Xaa_7$ is Thr;
$Xaa_8$ is Aib or Cys, with the proviso that when $Xaa_8$ is Cys, $Xaa_2$ is also Cys;
$Xaa_9$ is Leu or Ile;
$Xaa_{10}$ is Aib;
$Xaa_{11}$ is Pro;
$Xaa_{12}$ is Gln or Arg;
$Xaa_{13}$ is Aib;
$Xaa_{14}$ is Pro;
$Xaa_{15}$ is Aib;
$Xaa_{16}$ is Pro;
$Xaa_{17}$ is Phe; and
$Xaa_{18}$ is absent.

A particularly preferred aspect of the current invention provides a compound according to claim 16 that is:

$CH_3$-Trp-Aib-Gln-Aib-Ile-Thr-Aib-Leu-Aib-Pro-Gln-Aib-Pro-Aib-

Pro-Phe-COOH (SEQ ID NO 2).

The current invention also provides a pharmaceutical composition comprising a compound according to claim 1 in combination with a pharmaceutically acceptable carrier.

In addition, the current invention provides a method for administering a synthetic calcitonin mimetic to a patient in need of said mimetic, the method comprising administering to a patient a compound of claim 18.

Further, the current invention provides a method according to claim 19, wherein the administering step features oral administration.

DETAILED DESCRIPTION OF THE INVENTION

The synthetic calcitonin mimetics described herein are unique and quite different from native calcitonins, which are secreted by the thyroid and thymus glands of mammals and the ultimobranchial glands of lower vertebrates. Known, naturally occurring calcitonins are all 32-amino acid polypeptides having an amidated carboxy terminus and an intramolecular disulfide bond between cysteine residues in the 1 and 7 positions. The claimed synthetic calcitonin mimetics are small peptides containing up to 18 amino acid residues some of which are α-alkylated α-amino acids, such as 2-aminoisobutyric acid. They share little sequence homology with native calcitonins.

The synthetic calcitonin mimetics of the present invention are derived from a native calcitonin mimetic identified by a high throughput screen of natural product extracts, and described in pending U.S. patent application Ser. No. 08/416,602. This mimetic, 2807 B, contains α-alkylated α-amino acids distributed throughout the peptide, which can have the effect of reducing susceptibility to in vivo enzymatic breakdown, and contribute to the helical nature of the molecule. 2807 B is also hydrophobic and sterically hindered; both of these features enhance gastrointestinal absorption and resistance to proteolysis. Since one of the principal functions of the gastrointestinal tract is digestion of proteins and peptides, normal peptides used as oral therapeutic agents face some challenges which include the possibility of metabolism in both the gut and the intestinal lumen, poor transport across the intestinal mucosa, and rapid first-pass clearance in vivo, which may contribute to overall low bioavailability (Verhoef et al., *Eur. J. Drug Met. Pharmacokin.* 15:83–93, 1990; Aungst, *J. Pharm Sci.* 82:979–87, 1993).

To identify structural requirements of the calcitonin mimetics of the present invention, a series of analogs are synthesized wherein each individual residue is substituted with L-alanine (L-Ala scan). Essential residues are identified, and nonessential residues are targeted for modification or replacement by other residues that may enhance a desired quality (Ehrlich et al., *J. Biol. Chem.* 267:11606–11, 1992; Zhang et al., *Proc. Natl. Acad. Sci. USA* 90:4446–50, 1993). For example, arginine substitutions may be made, based on L-Ala scans, in as many positions as possible without reducing or losing potency of the peptide. Arginine is protonated at pH 7, and addition of arginine residues should increase the solubility of a peptide.

Structural and conformational information regarding each residue and the peptide as a whole is gained by synthesizing a series of analogs wherein each residue is substituted with D-alanine (D-Ala scan) (Galantino et al., in Smith, J. and Rivier, J. (eds.), Peptides Chemistry and Biology (Proceedings of the Twelfth American Peptide Symposium), ESCOM, Leiden, 1992, pp. 404–05). For example, D-Ala scans identify positions where D-amino acids can be substituted to increase metabolic stability.

C-terminal truncations can be done to determine the shortest active peptide, followed by deletions between the N- and C-terminus to determine shortest active sequence. Smaller peptides are likely candidates for increased oral bioavailability. Additions to further enhance bioavailability and activity may then be made to this active sequence, such as lipophilic random coils, or other active peptide segments to form a chimera, such as a mimetic-native calcitonin chimera.

Peptides can be modeled or designed to select analogs based on conformation or structure; for example, mimetics can be synthesized to increase homology with native calcitonin by inserting: Cys at positions $Xaa_2$ and $Xaa_8$, Ile at position $Xaa_9$, Leu at position $Xaa_6$, Arg at position $Xaa_{12}$, and Asn at position $Xaa_4$.

Conjugation with sugars (preferably glucose, glucosamine, galactose, galactosamine, mannose, mannosamine, maltose and the like) at the N- or C-terminus, at internal glutamine or threonine residues, or at the N-terminus by means of a succinyl linker, serves to stabilize certain conformational motifs, and may increase solubility and bioavailability of the peptide. Polyethylene glycol (PEG) conjugation at N- or C-terminus or on side chains can stabilize peptides and improve pharmacological performance (Delgado et al., *Crit. Rev. Ther. Drug Carrier Syst.* 9: 249–304, 1992). Such modifications may change the in vitro profile of a mimetic, but enhance circulating half-life and in vivo activity.

Helix stabilization can be accomplished by incorporating information from D-Ala scans, N-terminal succinylation, either alone or in combination with C-terminal cationization with arginine, morpholino or piperazino amines and lactambridge analogs. Conformational constraints can be introduced by cyclization, for example, by substituting cysteine residues at positions $Xaa_2$ and $Xaa_8$ to mimic native calcitonin.

Other methods known in the art to enhance stability, solubility, and bioavailability of peptides can be beneficially used within the present invention.

The following modifications can readily be made by skilled artisans to enhance desired features of a peptide, such as the synthetic calcitonin mimetics of the present invention. They serve to illustrate, not to limit, the choices available to those skilled in the art.

The N-terminus of a synthetic calcitonin mimetic can be substituted with a moiety termed "W", which can be hemisuccinimide or $R_1$—CO—. Suitable $R_1$ substituents include hydrogen; linear or branched alkyl, alkenyl, or alkynyl of not more than 32 carbon atoms; unsubstituted mono- or poly-cycloalkyl or mono- or poly-cycloalkylmethyl of not more than 20 carbon atoms, not more than 4 rings, each ring having 5–6 carbon atoms; unsubstituted mono- or poly-aryl or mono- or poly-arylmethyl of not more than 20 carbon atoms, not more than 4 rings, each ring having 5–6 carbon atoms; and unsubstituted mono- or poly-heteroaryl or mono- or poly-heteroarylmethyl of not more than 20 atoms, not more than 4 rings, each ring having 5–6 ring atoms and not more than 4 heteroatoms, in which the heteroatoms are selected from the group consisting of: N, O, and S.

Preferred linear or branched alkyl, alkenyl or alkynyl $R_1$ substituents include methyl, ethyl, propyl, isopropyl, butyl, lauryl, myristyl, palmitoyl, stearoyl, and valaryl, with lauryl particularly preferred.

Preferred unsubstituted mono- or poly-cycloalkyl or mono- or poly-cycloalkylmethyl $R_1$ substituents include cyclopentyl, cyclohexyl, cyclobutyl, cyclopropyl, cycloheptyl, decahydronaphthyl and admantyl, with cyclohexyl and admantyl particularly preferred.

Preferred unsubstituted mono- or poly-aryl or mono- or poly-arylmethyl $R_1$ substituents include benzyl, phenyl, biphenyl, naphthyl, anthranyl and fluorenyl, with phenyl, naphthyl, and biphenyl particularly preferred.

Preferred unsubstituted mono- or poly-heteroaryl or mono- or poly-arylmethyl $R_1$ substituents include indolyl, imidazolyl, furanyl, thiophenyl, benzofuranyl, pyrrolyl, benzimidazolyl, pyridinyl, bipyridinyl, benzothiophenyl, quinolinyl, tetrahydroisoquinolinyl, pyridylmethyl and imidazolylmethyl, with furanyl and imidazolyl particularly preferred.

Preferred aromatic rings of an unnatural aromatic amino acid include thiazolyl, thiophenyl, pyrazolyl, benzimidazolyl, naphthyl, furanyl, pyrrolyl, and pyridyl.

Preferred unnatural aromatic amino acids include β-2-thienyl-alanine, β-3-thienyl-alanine, β-1-naphthyl-alanine, β-2-naphthyl-alanine, β-2-pyridyl-alanine and β-3-pyridyl-alanine.

Preferred β-branched amino acids include Val, Ile, Thr, and allo-Thr.

Preferred aliphatic amino acids include Leu and Ala.

Preferred H-bond donor amino acids include Gln, Asn, His, Ser and Thr.

Amino acid $Xaa_1$ can be D- or L-Arg, D- or L-Lys, D- or L-Orn, or be absent. Preferably, $Xaa_1$ is Arg or absent, and most preferably $Xaa_1$ is absent.

Amino acid $Xaa_2$ can be a D- or L-aromatic amino acid, an unnatural aromatic amino acid, Cys, or be absent; with the proviso that when $Xaa_2$ is Cys, $Xaa_8$ is Cys or Pen. Preferably, $Xaa_2$ is Trp or Cys.

Amino acid $Xaa_3$ can be an α-alkylated α amino acid, a β-branched amino acid, or be absent; with the proviso that when $Xaa_{16}$ is 4-methyl proline, $Xaa_3$ is Aib or Iva. Preferably, $Xaa_3$ is Aib, Iva, Val, Ile, and most preferably $Xaa_3$ is Aib or Val.

Amino acid $Xaa_4$ can be Gln, Asn, His or a substituted amide ($R_2$—NH-Z). Preferably, $Xaa_4$ is Gln, Asn or His.

Amino acid $Xaa_5$ can be an α-alkylated α amino acid or a D-amino acid. Preferably, Xaa5 is Aib or Iva, and most preferably $Xaa_5$ is Aib.

Amino acid $Xaa_6$ can be a β-branched amino acid or an aliphatic amino acid; with the proviso that when $Xaa_6$ is Leu, $Xaa_9$ is Ile. Preferably, $Xaa_6$ is Ile or Leu.

Amino acid $Xaa_7$ can be a β-branched amino acid, an H-bond donor amino acid, or be absent; with the proviso that when $Xaa_7$ is absent, $Xaa_8$ is also absent. Preferably, $Xaa_7$ is Thr, allo-Thr or Ser, and most preferably $Xaa_7$ is Thr.

Amino acid $Xaa_8$ can be an α-alkylated α amino acid, a D-amino acid, Pen, Cys or be absent; with the proviso that when $Xaa_8$ is Cys, $Xaa_2$ is also Cys, or that when $Xaa_8$ is absent, $Xaa_9$ is also absent. Preferably, $Xaa_8$ is Aib or Cys.

Amino acid $Xaa_9$ can be a β-branched amino acid, an aliphatic amino acid, or be absent; with the proviso that when $Xaa_9$ is Ile, $Xaa_6$ is Leu, or that when $Xaa_9$ is absent, $Xaa_{10}$ is also absent. Preferably, $Xaa_9$ is Leu or Ile.

Amino acid $Xaa_{10}$ can be an α-alkylated α amino acid, a D-amino acid, or be absent; with the proviso that when $Xaa_{10}$ is absent, $Xaa_{11}$ is also absent. Preferably, $Xaa_{10}$ is Aib or Iva, and most preferably $Xaa_{10}$ is Aib.

Amino acid $Xaa_{11}$ can be Pro, pipecolic acid, thiazolidine carboxylic acid, 3- or 4-hydroxyproline, dehydroproline, 3- or 4-methylproline, 3,3-dimethylproline, N-alkyl alanine, or be absent; with the proviso that when $Xaa_{11}$ is absent, $Xaa_{12}$ is also absent. Preferably, $Xaa_{11}$ is Pro, 4-hydroxyproline, or absent, and most preferably $Xaa_{11}$ is Pro.

Amino acid $Xaa_{12}$ can be Gln, Asn, Arg, His, a substituted amide ($R_2$—NH-Z), or be absent. Preferably, $Xaa_{12}$ is Gln, Asn, Arg, His or absent, and most preferably $Xaa_{12}$ is Gln or Arg.

Amino acid $Xaa_{13}$ can be an α-alkylated α amino acid, a D-amino acid, or be absent; with the proviso that when $Xaa_{13}$ is absent, $Xaa_{14}$ is also absent. Preferably, $Xaa_{13}$ is Aib, Iva, or absent, and most preferably $Xaa_{13}$ is Aib.

Amino acid $Xaa_{14}$ can be Pro, pipecolic acid, thiazolidine carboxylic acid, 3- or 4-hydroxyproline, dehydroproline, 3- or 4-methylproline, 3,3-dimethylproline, N-alkyl alanine, or be absent; with the proviso that when $Xaa_{14}$ is absent, $Xaa_{15}$ is also absent. Preferably, $Xaa_{14}$ is Pro, 4-hydroxyproline, or absent, and most preferably $Xaa_{14}$ is Pro.

Amino acid $Xaa_{15}$ can be an α-alkylated α amino acid, a D-amino acid, or be absent; with the proviso that when $Xaa_{15}$ is absent, $Xaa_{14}$ is also absent. Preferably, $Xaa_{15}$ is Aib, Iva, or absent, and most preferably $Xaa_{15}$ is Aib.

Amino acid $Xaa_{16}$ can be Pro, pipecolic acid, thiazolidine carboxylic acid, 3- or 4-hydroxyproline, dehydroproline, 3- or 4-methylproline, 3,3-dimethylproline, N-alkyl alanine, or be absent; with the proviso that when $Xaa_{16}$ is Pro or 4-hydroxyproline, $Xaa_3$ is Aib, Iva, Val or Ile, and that when $Xaa_{16}$ is absent, $Xaa_{17}$ is also absent. Preferably, $Xaa_{16}$ is Pro, 4-hydroxyproline, or absent, and most preferably $Xaa_{16}$ is Pro.

Amino acid $Xaa_{17}$ can be a D- or L-aromatic amino acid, an unnatural aromatic amino acid, or be absent; with the proviso that when $Xaa_{17}$ is absent, $Xaa_{16}$ is also absent. Preferably, $Xaa_{17}$ is Phe or absent, and most preferably $Xaa_{17}$ is Phe.

Amino acid $Xaa_{18}$ can be Asp, Glu, or be absent. Preferably, $Xaa_{18}$ is Asp or absent, and most preferably $Xaa_{18}$ is absent.

The C-terminus of a synthetic calcitonin mimetic can be substituted with a moiety termed "Y", which can be $R_3$-Z or a substituted amide ($R_2$—NH-Z). Suitable $R_3$-Z substituents include, when Z is an aminoacyl radical of $Xaa_{17}$, $R_3$ is OH, $NH_2$, NH-PEG, or $NHCH_2(CH_2)_n$—$R_4$, wherein n=32 and $R_4$ is hydrogen or an α amino acid; or, alternatively, when Z is an α-aminoalkyl radical of $Xaa_{17}$, $R_3$ is COOH, $CONH_2$, $CH_2OH$, CONH-PEG, or $CONHCH_2(CH_2)_n$—$R_4$, wherein n=32 and $R_4$ is hydrogen or an α amino acid.

Suitable substituted amides ($R_2$—NH-Z) include, when Z is an α- or γ-acyl radical of $Xaa_{18}$, $R_2$ is polyethylene glycol (PEG); a linear or branched alkyl, alkenyl, or alkynyl of not more than 32 carbon atoms; an unsubstituted mono- or poly-cycloalkyl or mono- or poly-cycloalkylmethyl of not more than 20 carbon atoms, not more than 4 rings, each ring having 5–6 carbon atoms; an unsubstituted mono- or poly-aryl or mono- or poly-arylmethyl of not more than 20 carbon atoms, not more than 4 rings, each ring having 5–6 carbon atoms; or an unsubstituted mono- or poly-heteroaryl or mono- or poly-heteroarylmethyl of not more than 20 atoms, not more than 4 rings, each ring having 5–6 ring atoms, and not more than 4 heteroatoms, wherein the heteroatoms are selected from the group consisting of: N, O, and S.

A variety of modified calcitonins are known in the art, including calcitonins having amino acid substitutions (e.g., U.S. Pat. Nos. 4,824,936; 4,764,589; 4,663,309 and 4,658,014), deletions (e.g., U.S. Pat. Nos. 4,820,804; 4,764,591; 4,639,511; 4,605,514 and 4,537,716), truncations (Feyen et al., *Biochem. Biophys. Res. Comm.* 187:8–13, 1992), calcitonins containing D-amino acid substitutions (U.S. Pat. No. 4,652,627), modified by sugar and formyl residues (UK Patent No. 2,218,102A) or noncyclical analogs of calcitonin (Yates et al., *Endocrinology* 126:2845–49, 1990). All of these reported modifications were made directly to the sequences of either native human or salmon calcitonin, and bear little homology to the mimetics of the present invention.

The calcitonin mimetics of the present invention can be synthesized by solid phase or solution phase methods conventionally used for the synthesis of peptides (see, for example, Merrifield, R. B., *J. Amer. Chem. Soc.* 85:2149–54, 1963; Birr, C., *Aspects of the Merrifield Peptide Synthesis*, Springer-Verlag, Heidelberg, 1978; Carpino, L. A., *Acc. Chem. Res.* 6:191–98, 1973; Kent S. B., *Ann. Rev. Biochem.* 57:957–89, 1988; Gregg et al., *Int. J. Peptide Protein Res.* 55:161–214, 1990; *The Peptides, Analysis, Synthesis, Biology*, Vols. 1, 2, 3, 5: Gross, E and Meinhofer, J. (eds.), Acad. Press, New York, 1979; and Stewart et al., *Solid Phase Peptide Synthesis*, 2nd. ed., Pierce Chem. Co., Rockford, Ill., 1984; which are incorporated herein by reference in their entirety.) The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization (in the case of BOC chemistry, vide infra) and coupling of successive protected amino acid derivatives are used to link the amino acids from the C-terminus according to the amino acid sequence.

For some synthetic peptides, an FMOC strategy using an acid-sensitive resin may be used. Preferred solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydrylamine resin, and 4-(2',4'-dimethoxyphenyl-FMOC-aminomethyl)-phenoxyacetamidonorleucyl-MBHA resin (Rink amide MBHA resin). Acid sensitive resins, such as Sasrin and 2-chlorotrityl, are particularly preferred because they require mild acid cleavage, thus preventing possible cleavage of Aib-Pro bonds. In addition, acid-sensitive resins also provide C-terminal acids, if desired. A particularly preferred protecting group for α amino acids is base-labile 9-fluorenylmethoxycarbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys (Trit), FMOC-Ser(But), FMOC-Asn(Trit), FMOC-Leu, FMOC-Thr(Trit), FMOC-Val, FMOC-Gly, FMOC-Lys (Boc), FMOC-Gln(Trit), FMOC-Glu(OBut), FMOC-His (Trit), FMOC-Tyr(But), FMOC-Arg(PMC (2,2,5,7,8-pentamethylchroman-6-sulfonyl)), FMOC-Arg(BOC)$_2$, FMOC-Pro, and FMOC-Trp(BOC). The amino acid residues can be coupled by using a variety of coupling agents and chemistries known in the art, such as direct coupling with DIC (diisopropyl-carbodiimide), DCC (dicyclohexylcarbodiimide), BOP (benzotriazolyl-N-oxytrisdimethylaminophos-phonium hexafluorophosphate), PyBOP (benzotriazole-1-yl-oxy-tris-pyrrolidino phosphonium hexafluorophosphate), PyBrOP (bromo-tris-pyrrolidino-phosphonium hexafluorophosphate); via performed symmetrical anhydrides; via active esters such as pentafluorophenyl esters; or via performed HOBt (1-hydroxybenzotriazole) active esters or by using FMOC-amino acid fluoride and chlorides or by using FMOC-amino acid-N-carboxy anhydrides. Activation with HBTU ([2-(1H-benzotriazole-1-yl),1,1,3,3-tetramethyluronium hexafluorophosphate]) or HATU ([2-(1H-7-azabenzotriazole-1-yl),1,1,3,3-tetramethyluronium hexafluorophosphate]) in the presence of HOBt or HOAt (7-azahydroxybenztriazole) is preferred.

The solid phase method can be carried out manually, although automated synthesis on a commercially available peptide synthesizer (e.g., Applied Biosystems 431A or the like) is preferred. In a typical synthesis, the first amino acid (the C-terminal FMOC-Phe) is loaded on the chlorotrityl resin. Successive deprotection (with 20% piperidine/NMP (N-methylpyrrolidone)) and coupling cycles according to ABI FastMoc protocols (ABI user bulletins 32 and 33, Applied Biosystems Inc.) are used to build the whole peptide sequence. Double and triple coupling, with capping by acetic anhydride, may also be used.

The synthetic calcitonin mimetic peptide is cleaved from the resin and deprotected by treatment with TFA (trifluoroacetic acid) containing appropriate scavengers. Many such cleavage reagents, such as Reagent K (0.75 g crystalline phenol, 0.25 ml ethanedithiol, 0.5 ml thioanisole, 0.5 ml deionized water, 10 ml TFA) and others, can be used. Due to lability of Aib-Pro bonds, a preferred cleavage protocol uses 50% TFA/CH$_2$Cl$_2$ in ethanedithiol. The peptide is separated from the resin by filtration and isolated by ether precipitation. Further purification may be achieved by conventional methods, such as gel filtration and reverse phase HPLC (high performance liquid chromatography).

Synthetic calcitonin mimetics according to the present invention may be in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization out of the appropriate base.

All synthetic calcitonin mimetics are subjected to an assay system that permits rapid identification of substances having selective calcitonin receptor activity on cells expressing the calcitonin receptor. Only those modifications which retain calcitonin-like activity, as assayed by the CRE-luciferase assay for example, are within the scope of this invention. The calcitonin receptor is a member of the G-protein receptor family and transduces signal via activation of adenylate cyclase, leading to elevation of cellular cAMP levels (Lin et al., *Science* 254:1022–24, 1991). This assay system exploits the receptor's ability to elevate cAMP levels as a way to detect other molecules, not calcitonin, that are able to stimulate the calcitonin receptor and initiate signal transduction.

Receptor activation can be detected by: (1) measurement of adenylate cyclase activity (Salomon et al., *Anal. Biochem.* 58:541–48, 1974; Alvarez and Daniels, *Anal. Biochem.*

187:98–103, 1990); (2) measurement of change in intracellular cAMP levels using conventional radioimmunoassay methods (Steiner et al., *J. Biol. Chem.* 247:1106–13, 1972; Harper and Brooker, *J. Cyc. Nucl. Res.* 1:207–18, 1975); or (3) through use of a cAMP scintillation proximity assay (SPA) method (Amersham Corp., Arlington Heights, Ill.). While these methods provide sensitivity and accuracy, they involve considerable sample processing prior to assay, are time consuming, and involve the use of radioisotopes, and would be cumbersome for large scale screening assays.

An alternative assay system (described in pending U.S. patent application Ser. No. 08/100,887 which is incorporated herein in its entirety) involves selection of substances that are able to induce expression of a cyclic AMP response element (CRE)-luciferase reporter gene, as a consequence of elevated cAMP levels, in cells expressing a calcitonin receptor, but not in cells lacking calcitonin receptor expression. Such cells could include, for example, Boris/KZ10-3 (expressing hamster calcitonin receptor and a CRE-luciferase reporter gene in baby hamster kidney cells (BHK 570 cells)) or Hollex 1 (expressing human calcitonin receptor and a CRE-luciferase reporter gene in BHK cells, as described in pending U.S. patent application Ser. No. 08/100,887), calcitonin receptor negative cells such as KZ10-20-48 (calcitonin receptor negative BHK cell line expressing a CRE-luciferase reporter gene, described in pending U.S. patent application Ser. No. 08/100,887) or KZ10-20-48/pLJ6-4-25, which expresses the human glucagon receptor and a CRE-luciferase reporter gene in BHK cells. The human glucagon receptor is another member of the G-protein-coupled receptor family that transduces signal through adenylate cyclase-mediated elevation of cAMP.

This CRE-luciferase assay measures the end result of a multi-step signal transduction pathway triggered when a calcitonin mimetic stimulates the Gs-coupled calcitonin receptor. The complexity of this pathway provides multiple mechanisms for induction of luciferase transcription at points that are downstream of the calcitonin receptor, and therefore may not be calcitonin receptor-specific (e.g., forskolin's direct activation of adenylate cyclase). Any response triggered by non-specific inducers is eliminated by counter screening using the calcitonin receptor-negative cell lines described above.

Assessing the oral bioavailability and developing strategies to overcome limitations of a peptide candidate can be done by a number of methods well known in the art (Aungust, *J. Pharm. Sci.* 32:979–87, 1993). These include determining stability at acidic pH (pH 2.0, 37° C., 6 hrs.) and stability to enzymatic breakdown under conditions appropriate for the selected enzyme. Stability to enzymatic breakdown in liver and kidney homogenates and in serum can also be measured. Absorption and membrane transport can be determined from several in vitro models known in the art, including everted sacs, brush border membrane vesicles, intestinal rings, and several cell lines of renal (MDCK I, MDCK II and LLC-PK$_1$) or intestinal (T$_{84}$ and Caco-2) origin.

Well established animal models are available to test in vivo efficacy of calcitonin mimetics. For example, the hypocalcemic rat or mouse model can be used to determine the effect of synthetic calcitonin mimetics on serum calcium, and the ovariectomized rat or mouse can be used as a model system for osteoporosis. Bone changes seen in these models and in humans during the early stages of estrogen deficiency are qualitatively similar. Calcitonin has been shown to be an effective agent for the prevention of bone loss in ovariectomized women and rats (Mazzuoli et al., *Calcif. Tissue Int.* 47:209–14, 1990; Wronski et al., *Endocrinology* 129:2246–50, 1991). High dose estrogen has been shown to inhibit bone resorption and to stimulate bone formation in an ovariectomized mouse model (Bain et al., *J. Bone Miner. Res.* 8:435–42, 1993).

Synthetic calcitonin mimetics of the present invention are therefore contemplated to be advantageous for use in therapeutic applications for which calcitonin is useful. Such applications where calcitonin mimetics of the present invention may be used, for example, are in the treatment of osteoporosis, Paget's disease, hyperparathyroidism, osteomalacia, idiopathic hypercalcemia of infancy and other conditions. The synthetic calcitonin mimetics of the present invention can also be used to inhibit gastric secretion in the treatment of acute pancreatitis and gastrointestinal disorders, and as analgesics, in particular for bone pain.

Pharmaceutical compositions are administered at daily to weekly intervals. An "effective amount" of such a pharmaceutical composition is an amount that provides a clinically significant reduction in serum calcium, inhibition of bone resorption, or other beneficial effect. Such amounts will depend, in part, on the particular condition to be treated, age, weight, and general health of the patient, and other factors evident to those skilled in the art. Therapeutically effective doses of the calcitonin mimetics can vary widely depending on the indication, and are well known in the art. Therapeutic doses for the treatment of osteoporosis may range from 50–150 International Units (I.U.). Potency is estimated by comparing the hypocalcemic effect in rats with that of a standard preparation and is expressed in International Units, as described in the International Reference of Preparation, distributed by the National Institute for Biological Standards and Control, Holly Hill, London. Compounds having significantly enhanced half-lives may be administered at lower doses.

Synthetic calcitonin mimetics of the present invention can be formulated with a pharmaceutically acceptable carrier for parenteral, oral, nasal, rectal, or transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. One skilled in the art may formulate the compounds of the present invention in an appropriate manner, and in accordance with accepted practices, such as those disclosed in *Remington's Pharmaceutical Sciences*, Gennaro (ed.), Mack Publishing Co., Easton, Pa. 1990 (which is incorporated herein by reference in its entirety).

For use as an orally administered therapeutic, the oral absorption of the synthetic calcitonin mimetics can be further enhanced by use of drug permeation enhancers, such as salicylates; surfactants such as bile acids and their salts, polyoxyethylene fatty acids or fatty acyl ethers; chelating agents such as ethylenediamine tetraacetic acid; and solvents such as dimethylsulphoxide and ethanol (Verhoef et al., *Eur. J. Drug Metb. Pharmacokinet.* 15:83–93, 1990).

The invention is further illustrated by the following non-limiting examples.

EXAMPLES

Example 1

Synthesis of Synthetic Calcitonin Mimetics

The presence of 6 sterically hindered Aib residues, a stretch of sterically demanding couplings between Aib-Ile- Thr-Aib, and the susceptibility of Aib-Pro bonds to cleavage with TFA and other strong acids required use of a 2-chlorotrityl resin (Nova Biochem, La Jolla, Calif.) or Sasrin resin (Bachem Bioscience) from which the peptides could be cleaved using 50% TFA/dichloromethane ($CH_2Cl_2$) or milder acid conditions. Furthermore, synthesis required double and triple couplings followed by capping of any unreacted amines. Couplings needed to be monitored, and a few runs were needed to optimize the synthesis. The synthetic calcitonin mimetic Acetyl-Trp-Aib-Gln-Aib-Ile-Thr-Aib-Leu-Aib-Pro-Gln-Aib-Pro-Phe-COOH (SEQ ID NO 2) was synthesized on a 431A Peptide Synthesizer (Applied Biosystems, Inc., Foster City, Calif.) by solid phase strategy. The 2-chlorotrityl resin was loaded with FMOC-Phe. The FMOC-group was removed by treatment with 20% piperidine/NMP. FMOC-Pro was double coupled by using an HOBT/HBTU activating method in the presence of DIEA. This was followed by capping with $Ac_2O$/HOBT/DIEA. Successive deblocking of FMOC-group with piperdine, triple coupling of FMOC amino acids (except for residues $Xaa_8$ and $Xaa_{14}$) and capping with $Ac_2O$ provided the protected calcitonin mimetic linked to the resin. Cleavage from the resin and deprotection of the peptide was achieved with 50% TFA in dichloromethane containing 2.5% ethanedithiol for 30 minutes, then precipitated. The HPLC profile on a Vydac C18 column (Hewlett Packard, Wilmington, Del.) yielded a major peak at about 34% $CH_3CN/H_2O$/0.05% TFA. The crude yield was about 31%. The purification system used for isolation was a gradient from 20–80% $CH_3CN/H_2O$/0.05% TFA. The product eluted at 23 minutes. Structure was confirmed by mass spectroscopy and NMR.

In an alternative method, the FMOC-amino acids were preactivated by formation of HOAT esters, by pretreatment of FMOC-amino acids with PyBOP and HOAT. This synthesis was carried out using an Advanced Chem Tech 200.

Example 2

Calcitonin Mimetic Assay Development

A. Creation of CRE-Luciferase Cell Line: BHK/KZ10-20-48

Creation of this cell line is described in pending U.S. patent application Ser. No. 08/100,887 which is incorporated herein in its entirety. Briefly, a baby hamster kidney cell line, BHK 570 (deposited with the American Type Culture Collection, 12301 Parklawn Dr., Rockville, Md. under accession number CRL 10314), which does not express calcitonin receptor was identified. This cell line was transfected using calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973) with a plasmid pKZ10 (disclosed in pending U.S. patent application Ser. No. 08/100,887) encoding a luciferase reporter gene (de Wet et al., *Mol. Cell. Biol.* 7:725–37, 1987; Braiser et al., *Biotechniques* 7:1116–22, 1989) under the control of cAMP response elements (CRE) (Comb et al., *Nature* 323:353–56, 1986; Belegeane et al., *Mol. Cell. Biol.* 7:3994–4002, 1987; Roesler et al., *J. Biol. Chem.* 263:9063–66, 1988; Yamomoto et al., *Nature* 334:494–98, 1988; Montimny et al., *Metabolism* 39 (9, Suppl 2):6–12, 1990 and Habener et al, *Metabolism* 3.9. (9, Suppl 2):13–16, 1990), as well as a DHFR selectable marker. Stable transfectants were selected by growth in Dulbecco's modified Eagle's medium (DMEM) supplemented with 10% heat inactivated fetal bovine serum (HI-FBS), 2 mM L-glutamine and 1 mM sodium pyruvate containing 250 nM methotrexate (MTX) for 10–14 days. Clones were isolated, grown to confluence in opaque white microtiter plates (Dynatech, Chantilly, Va.), then treated with 25 mM forskolin, which elevates cellular cAMP through direct activation of adenylate cyclase (Berkowitz and Gilman, *Proc. Nat. Acad. Sci., USA*, 87:5258–62, 1990) for 4 hours at 37° C., 5% $CO_2$. Following incubation, cells were lysed and assayed for luciferase expression in a Labsystems Luminoskan microtiter luminometer (Labsystems Inc., Morton Grove, Ill.) using a Promega luciferase kit (E1500, Promega Corp., Madison, Wis.), as described below. Clones demonstrating significant induction of CRE-luciferase expression in response to forskolin, as compared to unstimulated (basal) luciferase expression, were retested, and clone KZ10-20-48, with a 20 fold (range 15–25 fold) induction of CRE-luciferase, was selected.

B. Creation of Human Calcitonin Receptor/CRE-Luciferase Cell Line: Hollex-1

Receptor positive cell line. KZ10-20-48 was tranfected, using calcium phosphate-mediated transfection (as described above), with pHollex encoding a human calcitonin receptor cDNA (cloned from a cDNA library derived from T47D human mammary tumor cells (ATCC, HBL 133), as described in pending U.S. patent application Ser. No. 08/100,887) and a neomycin selectable marker. Stable transfectants were selected following 10–12 days growth in DMEM supplemented with 10% HI-FBS, 2 mM L-glutamine, 1 mM sodium pyruvate, 250 nM MTX1 and containing 1 mg/ml G418. Clones were isolated, grown to confluence in opaque white Dynatech microtiter tissue culture plates, then treated with 1 mM human calcitonin or 25 mM forskolin for 4 hours at 37° C., 5% $CO_2$, and assayed for luciferase induction as described below. Clones demonstrating significant induction of CRE-luciferase in response to human calcitonin were rescreened following treatment with human calcitonin at concentrations ranging from 0.001–1000 nM, and clone Hollex-1 with a 20 fold (range 10–25 fold) induction of luciferase, a human calcitonin EC50 of 0.02 nM, and a forskolin EC50 of 1.2 mM, was selected for use in the high throughput screening assay for calcitonin mimetics.

Receptor negative cell line. KZ10-20-48 was also transfected with plasmid Zem 228 lacking the human calcitonin receptor gene, and the resulting transfectant pool, KZ10-20-48/Zem 228, was isolated for use as a receptor-negative specificity control for substances found to induce luciferase expression in Hollex 1 in the primary screen. Forskolin induces CRE-luciferase in KZ10-20-48/Zem 228 by 30 fold (range 20–35 fold) with an EC50 of 0.6 mM (range 0.5–1.5 mM), while human calcitonin at concentrations up to 1000 nM fails to induce CRE-luciferase levels above the basal level of expression Care was taken to select calcitonin receptor-positive and -negative clones that had similar CRE-luciferase inducibility, as demonstrated by forskolin dose responses that were essentially superimposable for the two cell lines. This criteria ensured that even small magnitude differences in response to test substances of calcitonin receptor-positive cells over calcitonin receptor-negative cells would be meaningful.

C. Creation of Hamster Calcitonin Receptor/Luciferase Cell Line: Boris/KZ10-3

An alternative cell line expressing the hamster calcitonin receptor was isolated for use in calcitonin mimetic screening. BHK 570 cells were transfected with the human cDNA library derived from T47D cells in plasmid vector Zem 228. Stable transfectants were isolated following 10–12 days growth in G418.

Colonies were tested for their ability to bind $^{125}$I-human calcitonin. The cells were plated at a density of $1\times10^5$ cells/well in a 24-well cell culture dish and allowed to grow for 48 hours at 37° C. and 5% $CO_2$ in DMEM supplemented with 10% HI-FBS, 2 mM L-glutamine, 1 mM sodium pyruvate, and 1 mg/ml G418. The cells were rinsed in binding medium (500 ml RPMI 1640 (Sigma, St. Louis, Mo.), 1 mg/ml BSA (Boehringer Mannheim, Indianapolis, Ind.)) to remove serum. Three hundred microliters of binding medium containing radiolabeled $^{125}$I human calcitonin (binding only or competition also) were added to appropriate wells. The cells were incubated for 1.5 hours at room temperature, and then rinsed 3 times with PBS to remove unincorporated radioactivity. Five hundred microliters of 1N NaOH was added to each well to solubilize the cells. The samples were collected from each well and CPMs were counted on a gamma counter.

One clone, Boris, with high calcitonin receptor expression was re-transfected with pKZ10, as described above, and stable transfectants were isolated following 10–14 days growth in DMEM supplemented with 10% HI-FBS, 2 mM L-glutamine, 1 mM sodium pyruvate, 250 nM MTX1 and 1 mg/ml G418. Clones were isolated and screened for induction of luciferase expression by human calcitonin or forskolin, as described below. Clone Boris/KZ10-3, with a 30 fold (range 25–40X1) induction of luciferase in response to human calcitonin, was selected for use in high throughput screening for calcitonin mimetics. Boris/KZ10-3 had a 25 fold (range 0.7–1.5 mM) response to forskolin (EC50=0.9 mM).

The human calcitonin receptor negative clone KZ10-20-48/Zem 228, described above, was used as a specificity check for substances found to induce luciferase expression in Boris/KZ10-3 during primary screens.

D. Creation of Human Glucagon Receptor/CRE-Luciferase Cell Line: KZ10-20-48/pLJ6-4-25

Test substances that appeared to specifically elevate luciferase expression in calcitonin receptor-positive cells, but not calcitonin receptor-negative cells, were subjected to an additional specificity check, i.e., their inability to activate other members of the G-protein coupled-receptor family. The glucagon receptor is another member of the G-protein coupled receptor family that transduces signal through adenylate cyclase mediated elevation of cAMP (Robison et al., Cyclic AMP, Academic Press, New York, 1971; Berridge, 1985; Jelinek et al., Science 259:1614–16, 1993). KZ10-20-48 was transfected, as above, with pLJ6' (deposited with the American Type Culture Collection (12301 ParkLawn Drive, Rockville, Md. 20852) under Accession Number 69183, as disclosed in pending U.S. patent application Ser. No. 08/086,631), containing the human glucagon receptor cDNA in plasmid pHZ-1, which also contains a DHFR selectable marker. Stable transfectants were selected in DMEM supplemented with 10% HI-FBS, 2 mM L-glutamine, 1 mM sodium pyruvate, 250 nM MTX1 and 1 mg/ml G418, and were screened for CRE-luciferase induction in response to 25 mM forskolin or 1000 nM human glucagon (Sigma), as described below. Clone KZ10-20-48/pLJ6-4-25 was selected for use in specificity confirmation. This clone exhibits a 35 fold induction of luciferase in response to human glucagon (EC50=0.2 nM) or forskolin (EC50=2.1 uM).

Example 3

CRE-Luciferase Assay Method for Calcitonin Mimetics

Receptor-positive and -negative cell lines were maintained by serial passage in growth medium (DMEM supplemented with 10% HI-FBS, 2 mM L-glutamine, 1 mM sodium pyruvate, 250 nM MTX, and 1 mg/ml G418). On the day prior to assay, cells were trypsinized, adjusted to $2\times10^5$ cells/ml in growth medium, plated in opaque white Dynatech Microlite microtiter tissue culture plates at 100 ul/well ($2\times10^4$ cells), and grown overnight to confluence, 37° C., 5% $CO_2$.

Test substances were prepared in $H_2O$ or DMSO at 100 times the final desired assay concentration. Induction was initiated by removing spent medium from the wells and adding 100 µl/well test substance diluted 1:100 or 1:1000 (first round screening extracts were diluted 1:1000) in assay medium (DMEM supplemented with 10% HI-FBS, 2 mM L-glutamine, 1 mM sodium pyruvate and 10 mM Hepes, pH 7.25). Controls were included on each plate: untreated wells (basal), 25 mM forskolin, and 100 nM human calcitonin. If test substances were prepared in DMSO, then an equal concentration of DMSO was included in control wells (not to exceed a final assay concentration of 2% DMSO, with a preferred maximum of 1%). Plates were incubated for 3 to 8 hours (4 hours preferred) at 37° C., 5% $CO_2$.

Following induction, luciferase activity was measured using a Promega luciferase assay kit (E1500) according to the assay kit protocol. Briefly, assay medium was removed and cells were washed once with phosphate buffered saline (PBS). After the wash, 25 ml of lysis buffer was added to each well, and the plates were incubated for 15 minutes at room temperature. The plates were transferred to a Labsystems Lumiscan microtiter luminometer which added 40 µl/well Luciferase Assay Substrate (Promega Corp.). The amount of luminescence (relative light units, RLU) was determined following a 1 second mix and a 1–3 second integration of signal. Basal (uninduced) luciferase signal was subtracted from all measurements, and the luciferase signal induced by test samples was expressed as a percentage of the signal in the calcitonin and forskolin controls. Specificity of the luciferase induction for calcitonin receptor-positive cell lines was determined by comparing the percent control values in the calcitonin receptor-positive lines (Hollex-1 or Boris/KZ10) to those observed in the calcitonin receptor-negative cell line (KZ10-20-48/Zem 228) and in the glucagon receptor-positive cell line (KZ10-20-48/pLJ6'-4). Samples inducing a signal over the basal level were selected for further characterization.

| CRE-Luciferase Induction | |
| --- | --- |
| Calcitonin Mimetic | EC50 (nM) |
| Synthetic 2807 (SEQ. ID. NO. 2) | 2276 |

For comparative purposes, the EC50 for human calcitonin is about 0.02 nM and for salmon calcitonin is about 0.006 nM.

Example 4

Direct cAMP Measurement by RIA/SPA Assay

Cell lines were prepared as in Example 3 above. At the time of assay, growth medium was removed and replaced with 50 µl/well of test sample, forskolin, or human calcitonin in assay medium (DMEM supplemented with 10% HI-FBS, 20 mM Hepes, pH 7.2, and 10 mM 3-Isobutyl-1-methylxanthine (IBMX) (Sigma)) pre-warmed to 37° C. Cells were incubated for 10 minutes at 37° C., 5% $CO_2$, followed by addition to each well of 200 µl water heated to just below the boiling point. After 15 minutes at room temperature, the supernatants were collected and transferred to a new microtiter plate and stored at −20° C. until assayed for cAMP. cAMP concentrations were determined using a radioimmunoassay scintillation proximity assay (SPA) kit (RPA 538) (Amersham Corp.) following the acetylation protocol described in the package insert. Alternatively, a conventional cAMP RIA assay may be used (Steiner et al., *J. Biol. Chem.* 247:1106–13, 1972; Harper and Brooker, *J. Cyc. Nucl. Res.* 1:207–18, 1975). The basal (uninduced) cAMP level in untreated cells was subtracted from all treated samples. The concentration of cAMP induced by test substances was expressed as a percentage of the cAMP concentration induced by forskolin or human calcitonin.

Example 5

Bone Resorption

A. Calvarial Assay

Calvaria from 4-day old neonatal CD-1 mice (pregnant mice received from Charles River Laboratories, Wilmington, Mass.) were trimmed with fine-tipped scissors to leave the parietal regions, including the sagittal suture. These trimmed bones were placed singly per well into 6-well cell culture cluster plates (Costar, Pleasanton, Calif.) with 1 ml/well of growth medium (DMEM (BioWhittaker, Walkersville, Md.) with 4.5 g/L glucose, 0.29 mg/ml L-glutamine, 1 mM sodium pyruvate, 15% heat-inactivated horse serum, and antibiotics (penicillin-G 50 mg/ml, streptomycin 50 mg/ml, and neomycin 100 mg/ml)), and rocked gently (RedRocker™, model PR50-115V) (Hoefer, San Francisco, Calif.) at 37° C. in a 5% $CO_2$ humidified incubator for 24 hours preincubation.

Following incubation, medium was removed and replaced with 1.5 ml/well of growth medium containing 1 nM parathyroid hormone (PTH) 1–34 (Sigma) to stimulate bone resorption. For evaluation of the ability of synthetic calcitonin mimetics to inhibit PTH induced bone resorption, mimetic compounds in DMSO were added to the growth medium at concentrations ranging from 1–240 mg/ml (final assay concentration of DMSO less than or equal to 1%). In each experiment human calcitonin (0.02–20 nM, 0.2–2 nM preferred) was added to PTH treated bones as a positive control. Control wells that did not receive PTH, human calcitonin or a synthetic calcitonin mimetic were included for determination of calcium release from untreated bones. All control wells contained a final assay concentration of DMSO equal to that present in the synthetic calcitonin mimetic treated wells.

Five bones were included in each sample group. Bones were incubated for 72 hours following PTH addition to allow resorption of bone to occur. Observations were made of the general appearance, healthiness and number of cells that migrate from the calvaria during the incubation as a possible indication of possible toxicity. Calvaria to be examined histologically were transferred to glass scintillation vials containing 10 ml of 10% neutral buffered formalin. The medium was removed from the wells, and total calcium measurements were made using a Nova 7/7+7 Electrolyte Analyzer (Nova Biomedical, Waltham, Mass.) according to the manufacturer's specifications. Induction of bone resorption by PTH was seen as an increase in the concentration of calcium in the growth medium due to degradation of the bone matrix. Human calcitonin and synthetic calcitonin mimetics inhibit this bone resorptive process as demonstrated by a lowering of the calcium in growth medium as compared to bones treated with PTH alone.

B. Calvaria Histology

To confirm the findings in the calvarial bone resorption assay employing calcium release from culture mouse calvariae, selected bones were fixed in 10% neutral buffered formalin and demineralized in 5% formic acid with 5% formalin. The bones were dehydrated through an ascending series of ethanol concentrations, infiltrated in glycol methacrylate, and embedded using a JB-4 embedding kit (PolySciences, Warrington, Pa.) (Liu and Kalu, *J. Bone Miner. Res.*, 5:973–82, 1990). Cross sections of calvariae cut at 5 mm were obtained and stained for tartrate-resistant acid phosphatase (TRAP) activity and counterstained with methyl green and thionin for cell morphology (Liu and Kalu, *J. Bone. Miner. Res.* 1990, supra). osteoclasts were identified by TRAP stain, multinucleation, large cell size, and irregular cell shape. The number of osteoclasts were counted from endocranial and ectocranial bone surfaces and expressed as number/mm perimeter. The size of all the osteoclasts counted was also measured using a Bone Morphometry program (Lui and Kalu, supra.; Bain et al., *J. Bone Miner. Res.* 8:435–42, 1993). This histomorphometric method demonstrated increases in the number and size of osteoclasts due to human parathyroid hormone (PTH 1–34) treatment. This PTH-induced increase was suppressed by treatment with human calcitonin.

Calcitonin mimetic compounds were evaluated in a similar fashion for their ability to suppress PTH-induced increases in osteoclast number and size. Cell toxicity (or death) was also evaluated morphologically. A low level of toxicity was indicated by the appearance of pyknotic nuclei in a small number of bone cells. With an increased level of nuclei, detachment of cells from bone surfaces, and losses of cytoplasmic stain and cell boundaries were observed. The osteocytic space also appeared empty.

TABLE 2

Effect of Calcitonin Mimetic on PTH Induced Bone Resorption in Mouse Calvariae

| Calcitonin Mimetic | Inhibition of Ca++ Release | |
|---|---|---|
| | EC50 (µM) | Histology |
| Synthetic 2807 | 36.0 | Inhibitory |

For comparative purposes, the EC50 for human calcitonin is about 0.2 to 0.5 nM.

Example 6

The Effect of Synthetic Calcitonin Mimetics on Bone Loss

The ability of calcitonin mimetics to prevent osteopenia induced by estrogen deficiency can be evaluated in the ovariectomized mouse model. Twenty-four female Swiss-Webster mice (8 weeks old) receive either an ovariectomy or sham surgery prior to the initiation of a 4 week treatment protocol. For the ovariectomy, a flank incision through the skin, muscle and abdominal peritoneum is made on each side, and the ovaries are located and dissected free of adherent fat and connective tissue, and excised. In the sham procedure the ovaries are exteriorized and replaced. In all animals the peritoneum and muscle are sutured together, and the skin incisions are closed with wound clips.

The calcitonin mimetic is dissolved in a minimal amount of dimethylsulfoxide and diluted in oil vehicle to a concentration of 50 mg/100 ml. The mice are treated daily for 4 weeks with a subcutaneous injection of calcitonin mimetic or oil vehicle according to the following outline: Sham/oil vehicle (SV); OVX1/oil vehicle; OVX1/50 mg calcitonin mimetic. There are 8 animals in each group.

At the conclusion of the 4-week calcitonin mimetic treatment, the mice are anesthetized with ether and sacrificed by cervical dislocation. Immediately after sacrifice, the femurs are removed and fixed in 70% ethyl alcohol (EtOH) and dehydrated undecalcified in a series of increasing alcohol concentrations using a VIP 2000 Automatic Tissue Processor (Miles Scientific, Elkart, Ind.): 80 and 95% EtOH, followed by three changes in 100% EtOH. After the final 100% EtOH, the femurs are cleared in two changes of xylene and then embedded in methylmethacrylate plastic according to previously described methods (Bain et al., *Stain Technology* 95: 159–63, 1990). Five micrometer frontal sections of the distal metaphyses are cut on a Reichert-Jung 2050 rotary microtome equipped with a tungsten-carbide knife. The 5 mm sections are mounted on glass slides and stained with Goldner's trichrome stain or stained for tartrate-resistant acid phosphatase activity, or unstained for evaluation of fluorochrome labels.

Histomorphometric measurements of the distal metaphyses are determined using the Bioquant Bone Morphometry Program (Biometrics, Inc., Nashville, Tenn.) interfaced via a camera lucida with an Olympus BH-2 light/epifluorescent microscope (Scientific Instruments, Inc., Redmond, Wash.). Morphometric measurements of cancellous bone volume (BV/TV) as well as other bone parameters are performed in the tissue space greater than 0.25 mm from the growth plate-metaphyseal junction to exclude primary spongiosa.

Example 7

Caco-2 Epithelial Transport

Caco-2 cells are human colon adenocarcinoma cells which, when grown in culture, differentiate to form monolayers that look and behave much like human small intestinal epithelium (Hidalog et al., *Gastroenterology* 96:736–49, 1989; Hilgers et al., *Pharm. Res.* 7:902–10, 1990). The Caco-2 monolayer system has been used as an in vitro model to study peptide transport across the intestinal mucosa (Conradi et al., *Pharm. Res.* 8:1453–60, 1991; Conradi et al., *Pharm. Res.* 9:435–39, 1992), and has shown a good correlation with intestinal absorption of peptides in rat (Conradi et al., *Pharm. Res.* 10:1790–92, 1993) and oral absorption of drugs in humans (Artursson and Karlsson, *Biochem. Biophys. Res. Commun.* 175:880–85, 1991).

To determine permeability and transport across the intestinal membrane, a Caco-2 monolayer can be grown on a microporous membrane (6.5 mm collagen-coated polyethylene terephthalate (PET) (Becton Dickson), 6.5 mm Transwell collagen-coated PTFE or Transwell polycarbonate membranes (Costar, Pleasanton, Calif.)). All membrane inserts are designed to fit into 24-well plates. Caco-2 cells (ATCC HTB-37) are propagated in Minimum Essential Medium (MEM) (GIBCO BRL, Gaithersberg, Md.) supplemented with 1% L-glutamine, 20% FBS and 1% MEM nonessential amino acid solution (GIBCO BRL). Filters are seeded at $4 \times 10^5$ cells/ml and grown for 6–25 days at 37° C., 5% $CO_2$. Monolayers are then placed in Hank's Balanced Salt Solution (GIBCO BRL) where 0.5 mCi/ml 1 mM transport chemical or $^3$H-synthetic mimetic (at various concentrations) is added to either the apical or basal side of the monolayer. Transport chemicals can include $^3$H-PEG, $^3$H-mannitol or $^{14}$C taucholic acid. Medium in the unlabeled chamber is changed every 15 minutes and analyzed using a LS6500 Multi Purpose Scintillation Counter (Beckman, Fullerton, Calif.). PEG has been shown to be relatively impermeable to Caco-2 monolayers, while mannitol more readily diffuses across the monolayer and designates a minimum permeability for orally available compounds. Taucholic acid has been shown to be directionally transported in an apical to basal direction in differentiated monolayers and could be used as a control.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa1 is D- or L-Arg, D- or L-Lys, D- or L-Orn, or absent with the proviso that whatever amino acid is the N terminal amino acid is substituted with hemisuccinimide, or R1-CO-, wherein R1 is selected from the group consisting of: hydrogen; linear or branched alkyl, alkenyl, or alkynyl of not more than 32 carbon atoms; unsubstituted mono- or poly- cycloalkyl or mono- or poly-cycloalkylmethyl of
not more than 20 carbon atoms, not more than 4 rings,
each ring having 5-6 carbon atoms; unsubstituted mono-
or poly-aryl or mono- or poly-arylmethyl of not more
than 20 carbon atoms, not more than 4 rings, each ring
having 5-6 carbon atoms; and unsubstituted mono- or
poly- heteroaryl or mono- or poly-heteroarylmethyl of
not more than 20 atoms, not more than 4 rings, each
ring having 5-6 ring atoms and not more than 4
heteroatoms, in which the heteroatoms are selected
from the group consisting of: N, O, and S."

( i x ) FEATURE:
    ( A ) NAME/KEY: Modified-site
    ( B ) LOCATION: 2
    ( D ) OTHER INFORMATION: /note="Xaa2 is a D- or L- aromatic
        amino acid, an unnatural aromatic amino acid, Cys, Pen,
        or absent, with the proviso that when Xaa2 is Cys or Pen,
        Xaa8 is Cys or Pen."

( i x ) FEATURE:
    ( A ) NAME/KEY: Modified-site
    ( B ) LOCATION: 3
    ( D ) OTHER INFORMATION: /note="Xaa3 is an a-alkylated a amino
        acid, a b- branched amino acid, or absent, with the
        proviso that when Xaa16 is 4-methyl proline, Xaa3 is
        Aib."

( i x ) FEATURE:
    ( A ) NAME/KEY: Modified-site
    ( B ) LOCATION: 4
    ( D ) OTHER INFORMATION: /note="Xaa4 is Gln, Asn, His, or a
        substituted amide (R2-NH-Z), wherein Z is an a- or
        g-acyl radical of Asn or Gln, and R2 is selected from a
        group consisting of: polyethylene glycol (PEG); linear
        or branched alkyl, alkenyl, or alkynyl of not more than
        32 carbon atoms; unsubstituted mono- or poly-cycloalkyl
        or mono- or poly-cycloalkylmethyl of not more than 20
        carbon atoms, not more than 4 rings, each ring having
        5-6 carbon atoms; unsubstituted mono- or poly-aryl or
        mono- or poly-arylmethyl of not more than 20 carbon
        atoms, not more than 4 rings, each ring having 5-6
        carbon atoms; and unsubstituted mono- or poly-heteroaryl
        or mono- or poly-heteroarylmethyl of not more than 20
        atoms, not more than 4 rings, each ring having 5-6 ring
        atoms, and not more than 4 heteroatoms, wherein the
        heteroatoms are selected from the group consisting of:
        N, O, and S."

( i x ) FEATURE:
    ( A ) NAME/KEY: Modified-site
    ( B ) LOCATION: 5
    ( D ) OTHER INFORMATION: /note="Xaa5 is an a-alkylated a amino
        acid, or a D- amino acid."

( i x ) FEATURE:
    ( A ) NAME/KEY: Modified-site
    ( B ) LOCATION: 6
    ( D ) OTHER INFORMATION: /note="Xaa6 is a b-branched amino
        acid, or an aliphatic amino acid."

( i x ) FEATURE:
    ( A ) NAME/KEY: Modified-site
    ( B ) LOCATION: 7
    ( D ) OTHER INFORMATION: /note="Xaa7 is a b-branched amino
        acid, an H- bond donor amino acid, or absent."

( i x ) FEATURE:
    ( A ) NAME/KEY: Modified-site
    ( B ) LOCATION: 8
    ( D ) OTHER INFORMATION: /note="Xaa8 is an a-alkylated a
        amino acid, a D-amino acid, Pen, Cys,or absent, with the
        proviso that when Xaa8 is Cys or Pen, Xaa2 is Cys or
        Pen."

( i x ) FEATURE:
    ( A ) NAME/KEY: Modified-site
    ( B ) LOCATION: 9
    ( D ) OTHER INFORMATION: /note="Xaa9 is a b-branched amino
        acid, an aliphatic amino acid, or absent."

( i x ) FEATURE:
    ( A ) NAME/KEY: Modified-site
    ( B ) LOCATION: 10
    ( D ) OTHER INFORMATION: /note="Xaa10 is an a-alkylated a amino
        acid, a D- amino acid, or absent."

( i x ) FEATURE:
    ( A ) NAME/KEY: Modified-site
    ( B ) LOCATION: 11
    ( D ) OTHER INFORMATION: /note="Xaa11 is Pro, pipecolic acid,
        thiazolidine carboxylic acid, 3- or 4-hydroxyproline,
        dehydroproline, 3- or 4-methylproline,
        3,3- dimethylproline, N-alkyl alanine, or absent."

( i x ) FEATURE:
    ( A ) NAME/KEY: Modified-site
    ( B ) LOCATION: 12
    ( D ) OTHER INFORMATION: /note="Xaa12 is Gln, Asn, Arg, His,
        absent, or a substituted amide (R2-NH-Z), wherein Z is
        an a- or g- acyl radical of Asn or Gln, and R2 is selected
        from a group consisting of: polyethylene glycol (PEG);
        linear or branched alkyl, alkenyl, or alkynyl of not more
        than 32 carbon atoms; unsubstituted mono- or poly-
        cycloalkyl or mono- or poly-cycloalkylmethyl of not more
        than 20 carbon atoms, not more than 4 rings, each ring
        having 5-6 carbon atoms; unsubstituted mono- or poly-aryl
        or mono- or poly-arylmethyl of not more than 20 carbon
        atoms, not more than 4 rings, each ring having 5-6 carbon
        atoms; and unsubstituted mono- or poly-heteroaryl or
        mono- or poly-heteroarylmethyl of not more than 20 atoms,
        not more than 4 rings, each ring having 5-6 ring atoms,
        and not more than 4 heteroatoms, wherein the heteroatoms
        are selected from the group consisting of: N, O, and S."

( i x ) FEATURE:
    ( A ) NAME/KEY: Modified-site
    ( B ) LOCATION: 13
    ( D ) OTHER INFORMATION: /note="Xaa13 is an a-alkylated a
        amino acid; a D-amino acid; or absent."

( i x ) FEATURE:
    ( A ) NAME/KEY: Modified-site
    ( B ) LOCATION: 14
    ( D ) OTHER INFORMATION: /note="Xaa14 is Pro, pipecolic acid,
        thiazolidine carboxylic acid, 3- or 4-hydroxyproline,
        3- or 4- methylproline, dehydroproline, 3,3-dimethyl-
        proline, N- alkyl alanine, or absent."

( i x ) FEATURE:
    ( A ) NAME/KEY: Modified-site
    ( B ) LOCATION: 15
    ( D ) OTHER INFORMATION: /note="Xaa15 is an a-alkylated
        a-amino acid, a D-amino acid; or absent."

( i x ) FEATURE:
    ( A ) NAME/KEY: Modified-site
    ( B ) LOCATION: 16
    ( D ) OTHER INFORMATION: /note="Xaa16 is Pro, pipecolic acid,
        thiazolidine carboxylic acid, 3- or 4-hydroxyproline,
        3- or 4- methylproline, dehydroproline, 3,3-dimethyl-
        proline, N- alkyl alanine, or absent."

( i x ) FEATURE:
    ( A ) NAME/KEY: Modified-site
    ( B ) LOCATION: 17
    ( D ) OTHER INFORMATION: /note="Xaa17 is a D- or L-aromatic
        amino acid; an unnatural aromatic amino acid; or absent."

( i x ) FEATURE:
    ( A ) NAME/KEY: Modified-site
    ( B ) LOCATION: 18
    ( D ) OTHER INFORMATION: /note="Xaa18 is Asp, Glu or absent,
        with the proviso that whatever amino acid occupies the C
        terminus the following C terminal substitutions are
        possible: hemisuccinimide, R3-Z, wherein, when Z is an
        aminoacyl radical of Xaa17, R3 is: OH, NH2, NH-PEG, or
        NHCH2(CH2)n- R4, wherein n=32 and R4 is hydrogen or an a
        amino acid; or wherein, when Z is an a-aminoalkyl
        radical of Xaa17, R3 is: COOH, CONH2, CONH-PEG, or CONHCH2(CH2)n-R4, wherein n=32 and R4 is hydrogen or an a amino acid; or a substituted amide (R2-NH-Z), wherein Z is an a- or g-acyl radical of Xaa18, and R2 is selected from a group consisting of: polyethylene glycol (PEG); linear or branched alkyl, alkenyl, or alkynyl of not more than 32 carbon atoms; unsubstituted mono- or poly-cycloalkyl or mono- or poly-cycloalkylmethyl of not more than 20 carbon atoms, not more than 4 rings, each ring having 5-6 carbon atoms; unsubstituted mono- or poly-aryl or mono- or poly-arylmethyl of not more than 20 carbon atoms, not more than 4 rings, each ring having 5-6 carbon atoms; and unsubstituted mono- or poly-heteroaryl or mono- or poly-heteroarylmethyl of not more than 20 atoms, not more than 4 rings, each ring having 5-6 ring atoms, and not more than 4 heteroatoms, wherein the heteroatoms are selected from the group consisting of: N, O, and S."

( x i ) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
1           5                   10                  15

Xaa Xaa ( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="N-terminal acetyl group (CH3)."

( i x ) FEATURE:
        ( A ) NAME/KEY: Modified-site
        ( B ) LOCATION: 2
        ( D ) OTHER INFORMATION: /note="All Xaa are Aib"

( i x ) FEATURE:
        ( A ) NAME/KEY: Modified-site
        ( B ) LOCATION: 16
        ( D ) OTHER INFORMATION: /note="C terminal has -COOH group."

( x i ) SEQUENCE DESCRIPTION: SEQ ID NO:2:

Trp Xaa Gln Xaa Ile Thr Xaa Leu Xaa Pro Gln Xaa Pro Xaa Pro Phe
1           5                   10                  15

What is claimed:

1. A compound of the formula W-X-Y, wherein:

W is hemisuccinimide, or $R_1$—CO—, wherein $R_1$ is selected from the group consisting of:

hydrogen, methyl, lauryl, phenyl, naphthyl, biphenyl, furanyl, imidazolyl, cyclohexyl and admantyl;

X is a peptide of 3–18 amino acid residues having the formula:
$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$ (SEQ ID NO 1) wherein:

$Xaa_1$ is D- or L-Arg,
D- or L-Lys,
D- or L-Orn, or
absent;

$Xaa_2$ is
a D- or L-aromatic amino acid,
an unnatural aromatic amino acid selected from the group consisting of: β-2-thienyl-alanine, β-3-thienyl-alanine, β-1-naphthyl-alanine, β-2-naphthyl-alanine, β-2-pyridyl-alanine and β-3-pyridyl-alanine;
Cys,
Pen, or
absent,
with the proviso that when $Xaa_2$ is Cys or Pen, $Xaa_8$ is Cys or Pen;

$Xaa_3$ is
an α-alkylated α amino acid,
a β-branched amino acid selected from the group consisting of: Val, Ile, Thr and allo-Thr, or
absent, with the proviso that when $Xaa_{16}$ is 4-methyl proline, $Xaa_3$ is Aib;

$Xaa_4$ is
Gln,

Asn,
His, or
a substituted amide ($R_2$—NH-Z), wherein Z is an α- or γ-acyl radical of Asn or Gln, and $R_2$ is selected from a group consisting of:
polyethylene glycol (PEG), methyl, lauryl, phenyl, naphthyl, biphenyl, furanyl, imidazolyl, cyclohexyl and admantyl;

$Xaa_5$ is
an α-alkylated α amino acid, or
a D-amino acid;

$Xaa_6$ is
a β-branched amino acid selected from the group consisting of: Val, Ile, Thr and allo-Thr, or
an aliphatic amino acid;

$Xaa_7$ is
a β-branched amino acid selected from the group consisting of: Val, Ile, Thr and allo-Thr,
an H-bond donor amino acid, or
absent;

$Xaa_8$ is
an α-alkylated α amino acid,
a D-amino acid,
Pen,
Cys, or
absent,
with the proviso that when $Xaa_8$ is Cys or Pen, $Xaa_2$ is Cys or Pen;

$Xaa_9$ is
a β-branched amino acid selected from the group consisting of: Val, Ile, Thr and allo-Thr,
an aliphatic amino acid, or
absent;

$Xaa_{10}$ is
an α-alkylated α amino acid,
a D-amino acid, or
absent;

$Xaa_{11}$ is
Pro,
pipecolic acid,
thiazolidine carboxylic acid,
3- or 4-hydroxyproline,
dehydroproline,
3- or 4-methylproline,
3,3-dimethylproline,
N-alkyl alanine, or
absent;

$Xaa_{12}$ is
Gln,
Asn,
Arg,
His,
absent, or
a substituted amide ($R_2$—NH-Z), wherein Z is an α- or γ-acyl radical of Ash or Gln, and $R_2$ is selected from a group consisting of:
polyethylene glycol (PEG), methyl, lauryl, phenyl, naphthyl, biphenyl, furanyl, imidazolyl, cyclohexyl and admantyl;

$Xaa_{13}$ is
an α-alkylated α amino acid;
a D-amino acid; or
absent;

$Xaa_{14}$ is
Pro,
pipecolic acid,
thiazolidine carboxylic acid,
3- or 4-hydroxyproline,
3- or 4-methylproline,
dehydroproline,
3,3-dimethylproline,
N-alkyl alanine, or
absent;

$Xaa_{15}$ is
an α-alkylated α-amino acid,
a D-amino acid; or
absent;

$Xaa_{16}$ is
Pro,
pipecolic acid,
thiazolidine carboxylic acid,
3- or 4-hydroxyproline,
3- or 4-methylproline,
dehydroproline,
3,3-dimethylproline,
N-alkyl alanine, or
absent;

$Xaa_{17}$ is
a D- or L-aromatic amino acid;
an unnatural aromatic amino acid selected from the group consisting of: β-2-thienyl-alanine, β-3-thienyl-alanine, β-1-naphthyl-alanine, β-2-naphthyl-alanine, β-2-pyridyl-alanine and β-3-pyridyl-alanine; or
absent;

$Xaa_{18}$ is
Asp,
Glu or
absent;

Y is
hemisuccinimide,
$R_3$-Z,
wherein, when Xaa18 is absent, Z is an aminoacyl radical of $Xaa_{17}$, $R_3$ is:
OH,
$NH_2$,
NH-PEG, or
$NHCH_2(CH_2)_n$—$R_4$, wherein n=32 and $R_4$ is hydrogen or an amino acid; or
a substituted amide ($R_2$—NH-Z), wherein Z is an α- or γ-acyl radical of $Xaa_{18}$, and $R_2$ is selected from a group consisting of:
polyethylene glycol (PEG), methyl, lauryl, phenyl, naphthyl, biphenyl, furanyl, imidazolyl, cyclohexyl and admantyl.

2. A compound according to claim 1 wherein the aliphatic amino acid is Leu or Ala.

3. A compound according to claim 1 wherein the H-bond donor amino acid is selected from the group consisting of: Gln, Asn, His, Ser and Thr.

4. A compound according to claim 1 wherein:
W is hemisuccinimide, or
$R_1$—CO—, wherein $R_1$ is methyl or hydrogen;
$Xaa_1$ is
Arg, or
absent;
$Xaa_2$ is
Trp, or
Cys;
with the proviso that when $Xaa_2$ is Cys, $Xaa_8$ is also Cys;

Xaa₃ is
  Aib,
  Iva,
  Val, or
  Ile;
Xaa₄ is
  Gln,
  Asn, or
  His;
Xaa₅ is
  Aib, or
  Iva;
Xaa₆ is
  Ile, or
  Leu;
Xaa₇ is
  Thr,
  allo-Thr, or
  Ser;
Xaa₈ is
  Aib, or
  Cys,
with the proviso that when Xaa₈ is Cys, Xaa₂ is also Cys;
Xaa₉ is
  Leu, or
  Ile;
Xaa₁₀ is
  Aib, or
  Iva;
Xaa₁₁ is
  Pro,
  4-hydroxyproline, or
  absent;
Xaa₁₂ is
  Gln,
  Asn,
  Arg,
  His, or
  absent;
Xaa₁₃ is
  Aib,
  Iva, or
  absent;
Xaa₁₄ is
  Pro,
  4-hydroxyproline, or
  absent;
Xaa₁₅ is
  Aib,
  Iva, or
  absent;
Xaa₁₆ is
  Pro,
  4-hydroxyproline, or
  absent;
Xaa₁₇ is
  Phe, or
  absent;
Xaa₁₈ is
  Asp, or
  absent; and
Y is
  R₃-Z,
wherein, when Xaa₁₈ is absent, Z is an aminoacyl radical of Xaa₁₇, R₃ is:
  OH,
  NH₂,
  NH-PEG, or
  NHCH₂(CH₂)$_n$—R4, wherein n=32 and R4 is hydrogen or an α amino acid.

5. A compound according to claim 4 wherein:
Xaa₁ is absent;
Xaa₂ is Trp or Cys, with the proviso that when Xaa₂ is Cys, Xaa₈ is also Cys;
Xaa₃ is Aib or Val;
Xaa₄ is Gln, Asn, or His;
Xaa₅ is Aib;
Xaa₆ is Ile or Leu;
Xaa₇ is Thr;
Xaa₈ is Aib or Cys, with the proviso that when Xaa₈ is Cys, Xaa₂ is also Cys;
Xaa₉ is Leu or Ile;
Xaa₁₀ is Aib;
Xaa₁₁ is Pro;
Xaa₁₂ is Gln or Arg;
Xaa₁₃ is Aib;
Xaa₁₄ is Pro;
Xaa₁₅ is Aib;
Xaa₁₆ is Pro;
Xaa₁₇ is Phe; and
Xaa₁₈ is absent.

6. A compound according to claim 5 that is:
CH₃-Trp-Aib-Gln-Aib-Ile-Thr-Aib-Leu-Aib-Pro-Gln-Aib-Pro-Aib-Pro-Phe-COOH (SEQ ID NO 2).

7. A pharmaceutical composition comprising a compound according to claim 1 in combination with a pharmaceutically acceptable carrier.

8. A method for administering a synthetic calcitonin mimetic to a patient in need of said mimetic, the method comprising administering to a patient a compound of claim 7.

9. A method according to claim 8 wherein the administering step is by oral administration.

10. A method for treating conditions associated with imbalances in bone homeostasis, comprising administering to a patient in need of such treatment a pharmaceutical composition of claim 7.

11. A method according to claim 10 wherein said condition is selected from the group consisting of: osteoporosis, Paget's disease and hyperparathyroidism.

12. A method of inhibiting bone resorption comprising administering to a patient in need of such inhibition a pharmaceutical composition of claim 7.

13. A method for providing an analgesic effect, comprising administering to a patient in need of such effect a pharmaceutical composition of claim 7.

14. A method according to claim 13, wherein said analgesic effect provides relief from bone pain.

15. A pharmaceutical composition according to claim 7, wherein said pharmaceutical composition is administered orally.

* * * * *